US007682789B2

(12) United States Patent
Chen et al.

(10) Patent No.: US 7,682,789 B2
(45) Date of Patent: Mar. 23, 2010

(54) METHOD FOR QUANTIFYING BIOMOLECULES CONJUGATED TO A NANOPARTICLE

(75) Inventors: Xiao-Bo Chen, Tucson, AZ (US); Christopher Bieniarz, Tucson, AZ (US); Michael Farrell, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 11/800,360

(22) Filed: May 4, 2007

(65) Prior Publication Data

US 2008/0274463 A1    Nov. 6, 2008

(51) Int. Cl.
  C12Q 1/68    (2006.01)
  G01N 33/53   (2006.01)
  C07K 14/00   (2006.01)
  C07H 21/00   (2006.01)
  C07H 21/02   (2006.01)
  C07H 21/04   (2006.01)

(52) U.S. Cl. ............... 435/6; 435/7.1; 530/350; 536/22.1; 536/23.1; 536/24.3

(58) Field of Classification Search .......... 435/6, 435/7.1; 536/23.1, 24.3; 530/387.1
See application file for complete search history.

(56) References Cited

U.S. PATENT DOCUMENTS

| 3,892,530 | A | * | 7/1975 | Felix et al. ............... 436/90 |
| 4,425,427 | A | * | 1/1984 | Luderer ................... 435/10 |
| 4,469,797 | A | | 9/1984 | Albarella |
| 4,879,224 | A | * | 11/1989 | Wallner et al. ............ 435/68.1 |
| 5,198,537 | A | | 3/1993 | Huber et al. |
| 5,447,841 | A | | 9/1995 | Gray et al. |
| 5,643,761 | A | | 7/1997 | Fisher et al. |
| 5,648,211 | A | | 7/1997 | Fraiser et al. |
| 5,648,245 | A | | 7/1997 | Fire et al. |
| 5,679,582 | A | * | 10/1997 | Bowie et al. ............ 436/518 |
| 5,731,171 | A | | 3/1998 | Bohlander |
| 5,756,696 | A | | 5/1998 | Gray et al. |
| 5,883,081 | A | * | 3/1999 | Kraus et al. ............. 514/44 |
| 6,057,099 | A | * | 5/2000 | Nathan et al. ............ 435/6 |
| 6,124,120 | A | | 9/2000 | Lizardi |
| 6,180,349 | B1 | * | 1/2001 | Ginzinger et al. ......... 435/6 |
| 6,207,299 | B1 | | 3/2001 | Krauth et al. |
| 6,218,152 | B1 | | 4/2001 | Auerbach |
| 6,235,480 | B1 | * | 5/2001 | Shultz et al. ............ 435/6 |
| 6,280,929 | B1 | | 8/2001 | Gray et al. |
| 6,280,949 | B1 | | 8/2001 | Lizardi |
| 6,291,187 | B1 | | 9/2001 | Kingsmore et al. |
| 6,322,901 | B1 | | 11/2001 | Bawendi et al. |
| 6,323,009 | B1 | | 11/2001 | Lasken et al. |
| 6,344,337 | B1 | * | 2/2002 | Mansfield et al. .......... 435/7.2 |
| 6,495,324 | B1 | | 12/2002 | Mirkin et al. |
| 6,506,564 | B1 | * | 1/2003 | Mirkin et al. ............ 435/6 |
| 6,569,621 | B1 | | 5/2003 | Cremer et al. |
| 6,576,291 | B2 | | 6/2003 | Bawendi et al. |
| 6,582,921 | B2 | * | 6/2003 | Mirkin et al. ............ 435/6 |
| 6,592,844 | B2 | | 7/2003 | Coombes et al. |
| 6,607,877 | B1 | | 8/2003 | Gray et al. |
| 6,617,137 | B2 | | 9/2003 | Dean et al. |
| 6,632,609 | B2 | | 10/2003 | Lizardi |
| 6,638,722 | B2 | | 10/2003 | Ji et al. |
| 6,642,034 | B2 | | 11/2003 | Lizardi |
| 6,649,138 | B2 | | 11/2003 | Adams et al. |
| 6,682,596 | B2 | | 1/2004 | Zehnder et al. |
| 6,696,304 | B1 | * | 2/2004 | Davies ................. 436/518 |
| 6,699,973 | B1 | * | 3/2004 | O'Mahony et al. ....... 530/387.9 |
| 6,750,016 | B2 | | 6/2004 | Mirkin et al. |
| 6,767,702 | B2 | | 7/2004 | Mirkin et al. |
| 6,797,474 | B2 | | 9/2004 | Lizardi |
| 6,815,064 | B2 | | 11/2004 | Treadway et al. |
| 6,828,097 | B1 | | 12/2004 | Knoll et al. |

(Continued)

FOREIGN PATENT DOCUMENTS

WO    WO 01/88089 A2    11/2001

(Continued)

OTHER PUBLICATIONS

Demers et al. A Fluorescence-based method for determining the surface coverage and hybridization efficiency of thiol-capped oligonucleotides bound to gold thin films and nanoparticles. Analytical Chemistry 72 : 5535-5541 (2000).*

(Continued)

Primary Examiner—Ethan Whisenant
(74) Attorney, Agent, or Firm—Klarquist Sparkman, LLP

(57) ABSTRACT

Disclosed embodiments concern quantifying a biomolecule conjugated to a nanoparticle. Quantifying typically comprises determining the number of biomolecules per nanoparticle. Any suitable biomolecule can be used, including but not limited to, amino acids, peptides, proteins, haptens, nucleic acids, oligonucleotides, DNA, RNA, and combinations thereof. A single type of biomolecule may be conjugated to the nanoparticle, more than one biomolecule of a particular class may be conjugated to the nanoparticle, or two or more classes of biomolecules may be conjugated to the nanoparticle. Certain disclosed embodiments comprise enzymatically or chemically digesting a biomolecule conjugated to the nanoparticle, or displacing a biomolecule using ligand-exchange chemistry. Where biomolecule concentrations are determined, any technique suitable for determining biomolecule concentration can be used, such as spectrophotometric techniques, including measuring tryptophan fluorescence and using a standard fluorescence intensity versus biomolecule concentration curve.

69 Claims, 11 Drawing Sheets
(1 of 11 Drawing Sheet(s) Filed in Color)

U.S. PATENT DOCUMENTS

| | | | |
|---|---|---|---|
| 6,921,496 | B2 | 7/2005 | Anderson et al. |
| 6,942,970 | B2 | 9/2005 | Isola et al. |
| 6,977,148 | B2 | 12/2005 | Dean et al. |
| 7,014,997 | B2 | 3/2006 | Knoll et al. |
| 7,045,504 | B2* | 5/2006 | Wilhelm et al. ............... 514/9 |
| 7,056,471 | B1* | 6/2006 | Han et al. .................. 420/523 |
| 7,285,289 | B2* | 10/2007 | Nagy et al. ................. 424/450 |
| 7,358,041 | B2* | 4/2008 | Short et al. .................... 435/4 |
| 2001/0051342 | A1 | 12/2001 | Farrell |
| 2002/0117659 | A1* | 8/2002 | Lieber et al. .................. 257/14 |
| 2003/0008414 | A1* | 1/2003 | Nie et al. ................... 436/524 |
| 2003/0022166 | A1 | 1/2003 | Collins et al. |
| 2003/0022243 | A1* | 1/2003 | Kondejewski et al. ........ 435/7.1 |
| 2003/0066998 | A1* | 4/2003 | Lee .............................. 257/19 |
| 2003/0165485 | A1* | 9/2003 | Bertilsson et al. .......... 424/94.6 |
| 2004/0077844 | A1* | 4/2004 | Jacobson et al. ......... 530/391.5 |
| 2004/0101822 | A1* | 5/2004 | Wiesner et al. ................. 435/5 |
| 2004/0115727 | A1* | 6/2004 | Steward et al. ............... 435/7.1 |
| 2004/0161742 | A1 | 8/2004 | Dean et al. |
| 2004/0214245 | A1* | 10/2004 | Schmitt et al. ............. 435/7.23 |
| 2004/0229300 | A1* | 11/2004 | Frederickson .............. 435/7.23 |
| 2004/0265897 | A1* | 12/2004 | Lizardi .......................... 435/6 |
| 2005/0012182 | A1 | 1/2005 | Jang et al. |
| 2005/0019901 | A1* | 1/2005 | Matveeva et al. ......... 435/287.2 |
| 2005/0048498 | A1 | 3/2005 | Woudenberg et al. |
| 2005/0054578 | A1* | 3/2005 | Sandberg et al. .............. 514/17 |
| 2005/0064488 | A1* | 3/2005 | Huh et al. ....................... 435/6 |
| 2005/0112636 | A1 | 5/2005 | Hurt et al. |
| 2005/0159432 | A1* | 7/2005 | Shepard et al. .......... 514/263.3 |
| 2005/0164213 | A1 | 7/2005 | Tabor et al. |
| 2005/0181394 | A1 | 8/2005 | Steemers et al. |
| 2006/0110744 | A1 | 5/2006 | Sampas et al. |
| 2006/0148124 | A1* | 7/2006 | Wilson ......................... 438/82 |
| 2006/0160116 | A1 | 7/2006 | Christian et al. |
| 2006/0246524 | A1* | 11/2006 | Bauer et al. ................. 435/7.92 |
| 2007/0057263 | A1* | 3/2007 | Kahen .......................... 257/79 |
| 2007/0099283 | A1* | 5/2007 | Mueller et al. .............. 435/223 |
| 2007/0117153 | A1* | 5/2007 | Bieniarz et al. .............. 435/7.1 |
| 2007/0274996 | A1* | 11/2007 | Carter et al. ............. 424/158.1 |
| 2008/0057513 | A1 | 3/2008 | Farrell |
| 2008/0268462 | A1* | 10/2008 | Kosmeder et al. ............ 435/7.1 |

FOREIGN PATENT DOCUMENTS

| | | |
|---|---|---|
| WO | WO 2005/001889 A2 | 6/2005 |
| WO | WO 2008/028156 A2 | 3/2008 |

OTHER PUBLICATIONS

Pathak et al., Hydroxylated quantum dots as luminescent probes for in situ hybridization. J of the American Chemical Society 123 : 4103-4104 (2001).*

Koh et al. Magnetic Iron Oxide Nanoparticles for Biorecognition : Evaluation of surface coverage and activity. Journal of Physical Chemistry 110: 1553-1558 (2006).*

Kim et al., A real-time PCR-based method for determining the surface coverage of thiol-capped oligonucleotides bound onto gold nanoparticles. Nucleic Acids Research 34(7) : e54 (2006).*

Tsugita et al., A rapid vapor-phase Acid (Hydrochloric Acid and Trifluoroacetic Acid ) Hydrolysis of Peptide and Protein. Journal of Biochemistry 102 : 1593-1597 (1987).*

Heid et al. , Real Time quantitative PCR. Genome Research 6 :986-994 (1996).*

Bellon. Quantitation and specific detection of collagenous proteins using an enzyme-linked immunosorent assay and an immunoblotting for cyanogen bromide peptides. Analytic Biochemistry 150: 188-202 (1985).*

Layne, E. Spectrophotometric and turbidimetric methods for measuring proteins. Methods in Enzymology 3 : 447-454 (1957).*

Woehrle et al., Thiol-functionalized, 1.5-nm gold nanoparticles through ligand exchange reactions : Scope and Mechanism of Ligand exchange. JACS 127 :2172-2183 (2005).*

Hickman et al., "Combining Spontaneous Molecular Assembly with Microfabrication to Pattern Surfaces: Selective Binding of Isonitriles to Platinum Microwires and Characterization by Electrochemistry and Surface Spectroscopy." *J. Am. Chem. Soc.*, vol. 111, pp. 7271-7272, 1989.

Matteucci et al., "Synthesis of Deoxyoligonucleotides on a Polymer Support." *J. Am. Chem. Soc.*, vol. 103, pp. 3185-3191, 1981.

Mucic et al., "Synthesis and characterization of DNA with ferrocenyl groups attached to their 5'-termini: electrochemical characterization of a redox-active nucleotide monolayer." *Chem. Commun.*, pp. 555-557, 1996.

* cited by examiner

Standard curve is generated using a series of different concentrations of free IgG treated the same as above Standard curve is generated using a series of different concentrations of free IgG treated the same as above Lane 1: Protein Marker
Lane 2: 0 µM IgG
Lane 3: 1 µM IgG
Lane 4: 2 µM IgG
Lane 5: 3 µM IgG
Lane 6: 4 µM IgG
Lane 7: 5 µM IgG
Lane 8: 1 µM Q655 GAM
Lane 9: 1 µM Q655 linker
Lane 10: 1 µM Q655

METHOD FOR QUANTIFYING BIOMOLECULES CONJUGATED TO A NANOPARTICLE

FIELD

Embodiments of a method for quantifying biomolecules conjugated to a nanoparticle are disclosed, with particular embodiments concerning determining numbers of protein and/or nucleic acid molecules per nanoparticle-biomolecule conjugate.

BACKGROUND

Nanoparticle-biomolecule conjugates are used for various purposes, including producing detectable signals in chemical and biological assays, such as immunohistochemistry (IHC) and in situ hybridization (ISH) assays. The efficiency of bioconjugates for such processes is determined, at least in part, by the number of biomolecules that are conjugated to each nanoparticle and available for whatever a particular purpose requires. For example, and with reference to using protein nanoparticle conjugates for in vitro diagnostics, one factor that determines bioconjugate efficiency is how many protein molecules are conjugated to a nanoparticle and available for binding target molecules.

As a first step in assessing bioconjugate efficiency, determination of the average number of biomolecules conjugated to nanoparticle can provide information that is needed to optimize a particular application of a bioconjugate. For example, antibody quantification, combined with tissue staining results, could provide information about the number of antibody molecules conjugated to a nanoparticle that provides the most specific and strongest staining in an IHC assay. An accurate method for determining biomolecule/nanoparticle ratios is highly desirable since it is not always the case that the more biomolecules conjugated to a nanoparticle the better.

SUMMARY

The present invention provides embodiments of a method for quantifying biomolecules conjugated to a nanoparticle. Quantifying includes determining any quantifiable feature of the biomolecule. For working embodiments, quantifying typically comprised determining concentrations of biomolecules displaced, and potentially digested, from the nanoparticle. The measured concentrations were then used to calculate the number of biomolecules per nanoparticle.

Disclosed embodiments of the present invention can be applied to bioconjugates having any suitable biomolecule, including but not limited to, amino acids, peptides, proteins, haptens, nucleic acids, oligonucleotides, DNA, RNA, and combinations thereof. A single type of biomolecule may be conjugated to the nanoparticle, more than one biomolecule of a particular class may be conjugated to the nanoparticle, and two or more classes of biomolecules may be conjugated to the nanoparticle.

Certain disclosed embodiments comprise enzymatically digesting biomolecules conjugated to the nanoparticle. For example, if the biomolecule is a protein, disclosed embodiments of the method use a proteolytic enzyme, or enzymes, such as an enzyme selected from proteinase K, trypsin, clostripain, staphylococcal protease, subtilisin, thrombin, chymotrypsin, carboxypeptidase a, pepsin, papain, cysteine proteases, serine proteases, aspartate proteases, and combinations thereof.

Biomolecules can be displaced and/or digested chemically, such as by using an acid. Proteins, for example, can be digested chemically using hydrochloric acid.

Biomolecules also can be displaced from nanoparticles by ligand exchange. Ligand exchange may be performed using ligand exchange compounds suitable for a particular bioconjugate, with exemplary ligand exchange compounds including amines, polyamines, phosphines, phosphine oxides, alkyl phosphines, derivatized alkyl phosphines, alkyl phosphine oxides, derivatized alkyl phosphine oxides, thiols, and combinations thereof. Furthermore, compounds also can have two different functional groups, each of which is useful for ligand exchange. Exemplary ligand exchange compounds include dithiothreitol, erythritol, dierythritol, trierythritol, pentaerythritol, dipentaerythritol, tripentaerythritol, dihydrolipoic acid.

For embodiments where biomolecule concentrations are determined, any technique suitable for determining biomolecule concentration can be used. Again with reference to working embodiments, biomolecule concentrations have been determined spectrophotometrically. For example, if the biomolecule is a protein, quantifying can comprise using tryptophan fluorescence and a standard curve of fluorescence intensity versus biomolecule concentrations to determine unknown concentrations of biomolecules obtained from a nanoparticle.

Certain disclosed embodiments also comprise reacting displaced biomolecules or digestion products of biomolecules with a detectable label. For example, with reference to proteins and production of digestion products having amine functional groups, such digestion products can be reacted with a detectable label, such that the reaction product becomes, for example a fluorophore or a chromophore Examples of such reagents include, but are not limited to, fluorescamine, (3-(4-carboxybenzoyl)quinoline-2-carboxaldehyde, o-phthaldialdehyde, and combinations thereof. Alternatively, certain reagents that are intrinsically fluorescent can be reacted with biomolecules or digestion products. These intrinsically fluorescent reagents include, again without limitation, reactive derivatives of Texas Red, fluorescein isothiocyanate, 2',7'-difluorofluorescein, coumarin, and combinations thereof. For these embodiments, the process may involve first separating excess detection reagent from products produced by reacting digestion products with the detection reagent, and thereafter determining biomolecule amounts.

Certain disclosed embodiments concern nucleic acid-nanoparticle conjugates, where the nucleic acid is, for example, a gene, viral RNA, viral DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural or synthetic nucleic acids, etc. One disclosed embodiment of the method for quantifying nucleic acids conjugated to a nanoparticle comprises providing a complementary nucleic acid strand labeled with a detectable moiety, such as a fluorophore. The nucleic acid-nanoparticle bioconjugate is then combined with the labeled, complimentary nucleic acid strand under conditions that allow the labeled strand to hybridize to the nucleic acid of the bioconjugate. A separation step may then be necessary to remove extraneous materials, such as non-hybridized complementary nucleic acid, or to remove and separate hybridization products from the nanoparticle.

For exemplary embodiments where the detectable moiety is a fluorophore, the fluorescence of the hybridization products can be measured. This fluorescence would be compared to standard concentration curves, generated using the same nucleic acid-complementary strand hybridization products, to determine nucleic acid concentrations, which could be converted to numbers of nucleic acid biomolecules conjugated to the nanoparticle. The intrinsic fluorescence contribution of certain quantum dots may interfere, or contribute to, the fluorescence of a sample comprising hybridization products. As a result, the fluorescence of the quantum dot fluorophore may need to be eliminated, such as by exposure to a quenching agent. Suitable quenching agents include acids, such as mineral acids. Alternatively, the quantum dot fluorescence may be quenched using nanomolar concentrations of transition metals.

Other detectable moieties also may be useful for determining numbers of nucleic acid molecules coupled to a nanoparticle for a particular biomolecule conjugate. For example, the complimentary strand may include a nucleic acid sequence that can be detected and measured by quantitative PCR techniques. This would provide a very sensitive technique for practicing the disclosed embodiments.

Nanoparticles are widely used in chemical and biochemical processes, and the present method is directed to all such nanoparticles, including without limitation, quantum dots, paramagnetic nanoparticles, superparamagnetic nanoparticles, metal nanoparticles, etc. Certain embodiments use alloyed quantum dots, including by way of example and without limitation, CdSe, ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN.

A particular disclosed working embodiment of the method comprised digesting and/or displacing protein, such as an immunoglobulin, from a first sample of a protein-Qdot nanoparticle to produce digested and/or displaced protein and non-conjugated nanoparticles. Nanoparticle were substantially separated from digested and/or displaced protein by centrifugation. Digested and/or displaced protein concentrations were determined using tryptophan fluorescence. A second sample of the protein-nanoparticle conjugate was then used for its intended purpose.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. Introduction

Figure 1:
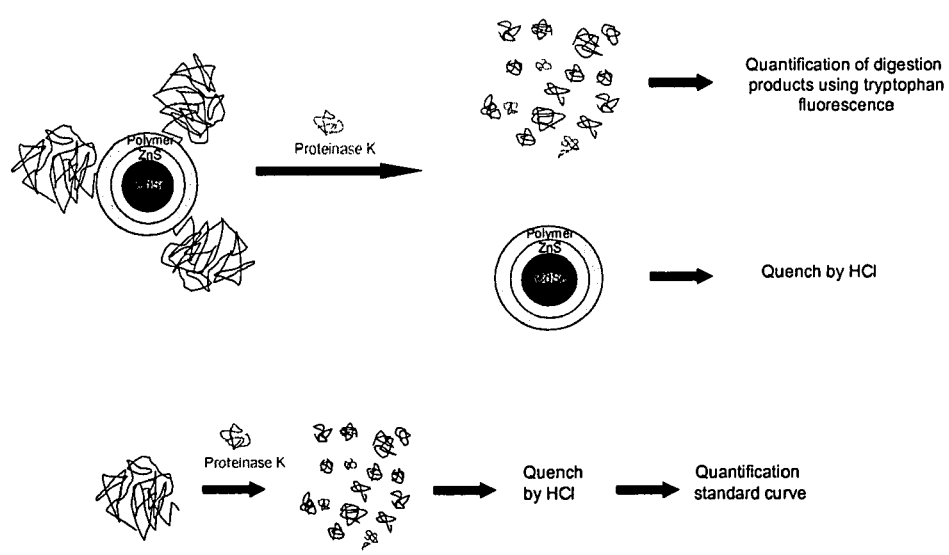
FIG. 1 schematically illustrates one embodiment of a method for quantifying proteins conjugated to a nanoparticle using enzymatic digestion and fluorescence spectroscopy.

The present invention provides embodiments of a method for quantifying biomolecules conjugated to nanoparticles, particularly proteins conjugated to nanoparticles. The method generally involves providing a bioconjugate comprising a nanoparticle having conjugated thereto at least one species of biomolecule, plural different biomolecules of the same class, or plural biomolecules of different classes. The biomolecule is displaced from the nanoparticle and optionally degraded to smaller constituent components either simultaneously with displacement from the nanoparticle, or subsequent to displacement. The amount of the biomolecule conjugated to the nanoparticle can be quantified after displacement from the nanoparticle using various different processes as disclosed herein, and processes similar thereto as would be understood by a person of ordinary skill in the art.

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting. All publications, patent applications, patents, and other references mentioned herein are incorporated by reference in their entirety, unless the context clearly indicates otherwise.

In order to facilitate review of the various examples of this disclosure, the following explanations of specific terms are provided:

Antibody: "Antibody" collectively refers to immunoglobulins or immunoglobulin-like molecules [including by way of example and without limitation, IgA, IgD, IgE, IgG and IgM, combinations thereof, and similar molecules produced during an immune response in any chordate such as a vertebrate, for example, in mammals such as humans, goats, rabbits and mice] and fragments thereof that specifically bind to a molecule of interest (or a group of highly similar molecules of interest) to the substantial exclusion of binding to other molecules. An "antibody" typically comprises a polypeptide ligand having at least a light chain or heavy chain immunoglobulin variable region that specifically recognizes and binds an epitope of an antigen. Immunoglobulins are composed of a heavy and a light chain, each of which has a variable region, termed the variable heavy ($V_H$) region and the variable light ($V_L$) region. Together, the $V_H$ region and the $V_L$ region are responsible for binding the antigen recognized by the immunoglobulin. Exemplary immunoglobulin fragments include, without limitation, proteolytic immunoglobulin fragments [such as $F(ab')_2$ fragments, Fab' fragments, Fab'-SH fragments and Fab fragments as are known in the art], recombinant immunoglobulin fragments (such as sFv fragments, dsFv fragments, bispecific sFv fragments, bispecific dsFv fragments, $F(ab)'_2$ fragments, single chain Fv proteins ("scFv"), and disulfide stabilized Fv proteins ("dsFv"). Other examples of antibodies include diabodies, and triabodies (as are known in the art), and camelid antibodies. "Antibody" also includes genetically engineered molecules, such as chimeric antibodies (for example, humanized murine antibodies), and heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Antigen: A compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

Avidin: Any type of protein that specifically binds biotin to the substantial exclusion of other small molecules that might be present in a biological sample. Examples of avidin include avidins that are naturally present in egg white, oilseed protein (e.g., soybean meal), and grain (e.g., corn/maize), and streptavidin, which is a protein of bacterial origin.

Bioconjugate or Conjugate: A compound having a nanoparticle, such as a quantum dot, and a biomolecule effectively coupled to the nanoparticle, either directly or indirectly, by any suitable means. For example, the biomolecule can be covalently or noncovalently (e.g. electrostatically) coupled to the nanoparticle. Indirect attachment of the biomolecule to the nanoparticle also is possible, such as by using a "linker" molecule, so long as the linker does not negatively affect the luminescence of the quantum dot or the function of the biomolecule. The linker preferably is bio-compatible. Common molecular linkers known in the art include a primary amine, a thiol, streptavidin, neutravidin, biotin, or similar compounds.

Biomolecule: Any molecule that may be included in a biological system, including but not limited to, a synthetic or naturally occurring protein, glycoprotein, lipoprotein, amino acid, nucleoside, nucleotide, nucleic acid, oligonucleotide, DNA, RNA, carbohydrate, sugar, lipid, fatty acid, hapten, and the like.

Conjugating, joining, bonding or linking: Coupling a first unit to a second unit. This includes, but is not limited to, covalently bonding one molecule to another molecule, non-covalently bonding one molecule to another (e.g. electrostatically bonding) (see, for example, U.S. Pat. No. 6,921,496, which discloses methods for electrostatic conjugation), non-covalently bonding one molecule to another molecule by hydrogen bonding, non-covalently bonding one molecule to another molecule by van der Waals forces, and any and all combinations of such couplings.

Detectable Label: A detectable compound or composition that is attached directly or indirectly to another molecule, such as an antibody or a protein, to facilitate detection of that molecule. Nanoparticles provide one, non-limiting example of a class of detectable labels.

Digest: Refers to any process whereby a biomolecule conjugated to a nanoparticle is converted into a different product, such as a constituent of a larger polymeric structure, such as an amino acid from a protein, or a nucleotide or oligonucleotide from a nucleic acid. By way of example, and without limitation, digest can refer to enzymatic digestion of a biomolecule, chemical digestion, such as using an inorganic or organic acid, physical digestion, and combinations thereof.

Fluorogen: A molecule that is not fluorescent, but which becomes fluorescent following a physical change or a chemical reaction, including a reaction with a second molecule.

Hapten: A molecule, typically a relatively small molecule, that can combine specifically with an antibody, but typically is substantially incapable of being immunogenic except in combination with a carrier molecule.

Isolated: An "isolated" biological component (such as a biomolecule) has been substantially separated or purified away from other components in a mixture.

Molecule of interest or Target: A molecule for which the presence, location and/or concentration is to be determined. Examples of molecules of interest include proteins and nucleic acid sequences tagged with haptens.

Nanoparticle: A nanoscale particle with a size that is measured in nanometers, for example, a nanoscopic particle that has at least one dimension of less than about 100 nm. Examples of nanoparticles include, by way of example and without limitation, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. A nanoparticle can produce a detectable signal, for example, by photon emission (including radio frequency and visible photons).

Nucleic Acid: Examples of nucleic acids include genes (e.g., a gene associated with a particular disease), viral RNA and DNA, bacterial DNA, fungal DNA, mammalian DNA, cDNA, mRNA, RNA and DNA fragments, oligonucleotides, synthetic oligonucleotides, modified oligonucleotides, single-stranded and double-stranded nucleic acids, natural and synthetic nucleic acids, etc.

Polypeptide: A polymer in which the monomers are amino acid residues which are joined together through amide bonds. When the amino acids are α-amino acids, either the L-optical isomer or the D-optical isomer can be used. The terms "polypeptide" or "protein" as used herein are intended to encompass any amino acid sequence and include modified sequences such as glycoproteins. "Polypeptide" covers naturally occurring proteins, as well as those which are recombinantly or synthetically produced. "Residue" or "amino acid residue" includes an amino acid that is incorporated into a protein, polypeptide, or peptide.

Protein: A molecule comprised of amino acids. The distinction between peptides and proteins typically involves size or length; that is peptides are shorter than proteins. There are several different conventions used to determine if a molecule is a peptide or a protein. For purposes of this application, in order for a polypeptide to be a protein, it typically has some in vivo biological function. Another convention places an informal dividing line at approximately 50 amino acids, i.e. amino acid chains having 50 or fewer amino acids are peptides, and chains having 51 or more amino acids are proteins. Because of the arbitrary nature of this definition, a person of ordinary skill in the art might also consider that peptides are amino acid polymers that do not have a defined secondary structure, whereas proteins have defined secondary structures. By this definition, the same molecule can be either a peptide or a protein depending on its environment.

Purified: The term "purified" does not require absolute purity; rather, it is intended as a relative term. Thus, for example, a purified peptide, protein, conjugate, or other compound is one that is isolated in whole or in part from proteins or other constituents of a mixture. Generally, substantially purified peptides, proteins, conjugates, or other active compounds for use within the disclosure comprise more than 80% of all macromolecular species present in a preparation prior to admixture or formulation of the peptide, protein, conjugate or other active compound with a pharmaceutical carrier, excipient, buffer, absorption enhancing agent, stabilizer, preservative, adjuvant or other co-ingredient. More typically, the peptide, protein, conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Quantum dot: A nanoscale particle that exhibits size-dependent electronic and optical properties due to quantum confinement. Quantum dots have, for example, been constructed of semiconductor materials (e.g., cadmium selenide and lead sulfide) and from crystallites (grown via molecular beam epitaxy), etc. Quantum dots are described in the patent literature [see, for example, U.S. Pat. Nos. 6,207,299, 6,322, 901, 6,576,291, 6,649,138 (surface modification methods in which mixed hydrophobic/hydrophilic polymer transfer agents are bound to the surface of the quantum dots), U.S. Pat. Nos. 6,682,596, 6,815,064 (for alloyed or mixed shells), each of which patents is incorporated by reference herein)], and in the technical literature [such as "Alternative Routes toward High Quality CdSe Nanocrystals," (Qu et al., Nano Lett., 1(6):333-337 (2001)]. Quantum dots having various surface chemistries and fluorescence characteristics are commercially available from Invitrogen Corporation, Eugene, Oreg., Evident Technologies (Troy, N.Y.), and Quantum Dot Corporation (Hayward, Calif.), amongst others.

"Quantum dot" also includes alloyed quantum dots, such as ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN. Alloyed quantum dots and methods for making the same are disclosed, for example, in US Application Publication No. 2005/0012182 and PCT Publication WO 2005/001889.

Sample: A biological specimen comprising tissue or a biomolecule, such as genomic DNA, RNA (including mRNA), amino acids, peptides, proteins, or combinations thereof, obtained from a subject. Examples include, but are not limited to, peripheral blood, urine, saliva, tissue biopsy, surgical specimen, amniocentesis samples and autopsy material.

Subject: Includes both human and veterinary subjects, for example, humans, non-human primates, dogs, cats, horses, and cows.

III. Bioconjugates

A. Generally

Biomolecules can be conjugated to any nanoparticle to form bioconjugates within the scope of the present invention. Nanoparticles can be selected for a particular purpose, such as for producing a detectable signal useful for IHC or ISH. Exemplary nanoparticles for the present invention include, without limitation, metal or metal alloy nanoparticles, such as metal nanoparticles generally, including gold and silver nanoparticles, nanoclusters, nanorods, nanotubes, nanowires, nanowire self assemblies, nanospheres, functional biomedical nanoparticles, and quantum dots. Additional exemplary nanoparticles are disclosed in *Nanoparticles*, by Günther Schmidt (Wiley-BCH, 2004), which is incorporated herein by reference. Several working embodiments of the present invention have used quantum dot nanoparticles, such as Q605 and Q655 quantum dot nanoparticles (available from Invitrogen Corporation, Eugene, Oreg.), where the number used in such nomenclature refers to the approximate wavelength of the emission maximum of the nanoparticle. Thus, quantum dots can be selected to provide a detectable signal at a particular wavelength.

The present invention is directed to all potential biomolecules that may be conjugated to a nanoparticle. For most applications, the biomolecule(s) is/are amino acid/peptide/ protein or nucleoside/nucleotide/nucleic acid. Specific exemplary biomolecules useful for making bioconjugates include, without limitation: monoclonal or polyclonal antibodies, such as IgA, IgD, IgE, IgG, IgM; antibody fragments that specifically bind to a molecule of interest (or a group of highly similar molecules of interest) to the substantial exclusion of binding to other molecules including, without limitation, proteolytic antibody fragments [such as $F(ab')_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, $F(ab)'_2$ fragments, single chain Fv proteins ("scFv"), and disulfide stabilized Fv proteins ("dsFv"). Other useful biomolecules include diabodies, triabodies, and camelid antibodies; genetically engineered antibodies, such as chimeric antibodies, for example, humanized murine antibodies); heteroconjugate antibodies (such as, bispecific antibodies); streptavidin; receptors; enzymes; BSA; polypeptides; aptamers; and combinations thereof.

B. Making Bioconjugates

Bioconjugates, like nanoparticles, are commercially available. Alternatively, bioconjugates first can be synthesized before determining the numbers of biomolecules conjugated to the nanoparticle as a result of the synthesis according to disclosed embodiments of the present invention. Methods for making biomolecule conjugates are generally known in the art, and useful bioconjugates can be made by any suitable method. Exemplary methods for making biomolecule-nanoparticle conjugates are summarized below.

1. Peptide/Protein-Nanoparticle Conjugates

Exemplary methods for making protein-nanoparticle conjugates are disclosed in various United States patents, such as U.S. Pat. No. 6,592,844. One method disclosed by the '844 patent concerns mixing an aqueous solution of at least one protein or modified protein with an aqueous solution of at least one α-hydroxy acid or analogue or derivative thereof, adding to the mixture a coacervation agent, which results in the formation of microspheres incorporating the protein or modified protein, removing the coacervation agent, and recovering microspheres from the aqueous solution.

2. Nucleic Acid-Nanoparticle Conjugates

Oligonucleotide conjugates are disclosed in a number of issued U.S. patents, including U.S. Pat. Nos. 6,495,324, 6,750,016 and 6,767,702. According to the '702 patent, nanoparticles, oligonucleotides or both are functionalized in order to attach the oligonucleotides to the nanoparticles, according to methods known in the art. For instance, oligonucleotides functionalized with alkanethiols at their 3'-termini or 5'-termini readily attach to gold nanoparticles. Whitesides, Proceedings of the Robert A. Welch Foundation 39th Conference on Chemical Research Nanophase Chemistry, Houston, Tex., pages 109-121 (1995); Mucic et al. *Chem. Commun.* 555-557 (1996) (describes a method for attaching 3' thiol DNA to nanoparticles). The alkanethiol method also can be used to attach oligonucleotides to other metal, semiconductor and magnetic colloids and to the other nanoparticles listed above. Other functional groups for attaching oligonucleotides to solid surfaces include: phosphorothioate groups and substituted alkylsiloxanes (see, for example, Burwell, Chemical Technology, 4, 370-377 (1974) and Matteucci and Caruthers, *J. Am. Chem. Soc.*, 103, 3185-3191 (1981); disulfides; sulfolanes and sulfoxides (see, for example, Hickman et al., *J. Am. Chem. Soc.*, 111, 7271 (1989); isonitriles; silanes; phosphates; and combinations thereof.

IV. Quantifying Numbers of Biomolecule Conjugated to Nanoparticle Generally

A. Biomolecule Displacement and/or Digestion

In general, the first step in disclosed embodiments is to separate biomolecules from the nanoparticle to which they are conjugated, followed by determining the numbers of biomolecules obtained per nanoparticle. Certain embodiments of the present invention displace the biomolecule either simultaneously with or followed by a digestion process to produce smaller constituent units (such as peptides and amino acids) from larger polymeric units. This is then followed by quantifying the numbers of smaller molecules per nanoparticle.

Digestion can be done by any suitable method, as will be understood by a person of ordinary skill in the art, including but not limited to, enzymatic digestion, chemical digestion, physical digestion, and combinations thereof. A person of ordinary skill in the art will appreciate that there are a number of enzymes suitable for enzymatic digestion of biomolecules, such as proteins and/or nucleic acids. Suitable examples of protease enzymes useful for proteolytic digestion of proteins conjugated to a nanoparticle include proteinase K, trypsin, clostripain, staphylococcal protease, thrombin, chymotrypsin, carboxy peptidase a, and combinations thereof.

Peptides and proteins also can be digested by any suitable chemical means. Exemplary chemical methods include, but are not limited to, Edman digestion, treatment with mineral acids such as hydrochloric acid, nitric acid, sulphuric acid, treatment with organic acids, such as trifluoroacetic acid, etc. Edman digestion can be practiced using small amounts of the peptide or protein, such as about 10 picomoles. Another method for chemically digesting proteins comprising methionine involves using cyanogen bromide. Very little cyanogen bromide is required to quantitatively cleave proteins and peptides. And, unlike most proteases, which are usually used to cleave peptides, cyanogen bromide cleaves a peptide cleanly at the C-side of methionine residues.

For embodiments involving nucleic acids, digestion is not a required, nor a desirable, step. One disclosed embodiment of the method for quantifying nucleic acids conjugated to a nanoparticle comprises providing a complementary nucleic acid strand labeled with a detectable moiety, such as a fluorophore. The nucleic acid-nanoparticle bioconjugate is then combined with the labeled, complimentary nucleic acid strand under conditions that allow the labeled strand to hybridize to the nucleic acid of the bioconjugate. A separation step may then be necessary to remove extraneous materials, such as non-hybridized complementary nucleic acid, or to remove and separate hybridization products from the nanoparticle.

For exemplary embodiments where the detectable moiety is a fluorophore, the fluorescence of the hybridization products could be measured. This fluorescence would be compared to standard concentration curves, generated using the same nucleic acid-complementary strand hybridization products, to determine nucleic acid concentrations, which could be converted to numbers of nucleic acid biomolecules conjugated to the nanoparticle. The intrinsic fluorescence contribution of certain quantum dots may interfere, or contribute to, the fluorescence of a sample comprising hybridization products. As a result, the fluorescence of the quantum dot fluorophore may need to be reduced or eliminated, such as by exposure to a quenching agent. Suitable quenching agents include acids, such as mineral acids. Alternatively, the quantum dot fluorescence may be quenched using nanomolar concentrations of transition metals.

Other detectable moieties also may be useful for determining numbers of nucleic acid molecules coupled to a nanoparticle for a particular biomolecule conjugate. For example, the complimentary strand may include a nucleic acid sequence that can be detected and measured by quantitative PCR techniques. This would provide a very sensitive technique for practicing the disclosed embodiments.

B. Quantifying Displaced/Degraded Biomolecules

Following obtaining biomolecules from a biomolecule-nanoparticle bioconjugate, such as by separation of the biomolecule from the nanoparticle, and optionally digestion of the biomolecule, certain disclosed embodiments thereafter determine concentrations of displaced biomolecules. This can be done by a number of suitable methods. For certain working embodiments, biomolecule concentrations were determined spectrophotometrically using a standard concentration curve. Standard concentration curves can be prepared using methods known to a person of ordinary skill in the art. Briefly, standard concentration curves may be prepared by measuring the signals obtained from samples comprising the same biomolecules to be displaced from a nanoparticle but at various different concentrations. Plotting signal versus concentration for known concentrations of the biomolecule produces a standard concentration versus signal curve. A sample of the biomolecule(s) displaced from the nanoparticles is obtained, a measurement is made, and the results compared to the standard curve to determine the concentration of biomolecules in the sample.

One useful method for quantifying protein is tryptophan fluorescence. Tryptophan strongly absorbs light at about 270 nanometers to about 280 nanometers. Tryptophan emits light at a wavelength of approximately 300-400 nanometers, with a maximum fluorescence emission at about 350 nanometers.

Other spectrophotometric process also can be used. For example, certain working embodiments have first degraded a protein to produce peptides and/or amino acids having free amine groups. Amine groups are relatively reactive, and hence can be reacted with a suitable detectable moiety. Exemplary detectable moieties that react with these free amines include fluorescamine, (3-(4-carboxybenzoyl)quinoline-2-carboxaldehyde, and o-phthaldialdehyde. Certain reagents are intrinsically fluorescent. These intrinsically fluorescent reagents also can be used to detect digestion products and include, without limitation, reactive derivatives of Texas Red, fluorescein isothiocyanate, 2',7'-difluorofluorescein, coumarin, and combinations thereof. For these embodiments, the process involves first separating excess detection reagent from products produced by reacting digestion products with the detection reagent, and thereafter determining biomolecule amounts.

Other common laboratory techniques also can be used to quantify biomolecules. Chromatographic techniques, such as liquid chromatography, are useful processes for quantifying biomolecules. For example, preparatory chromatography could be used to separate desired compounds for quantification from extraneous materials, and then HPLC used, and the area under a detection peak determined, to quantify concentrations of biomolecule in a sample.

V. Reference to Exemplary Working Embodiments

FIG. 1 schematically illustrates one working embodiment of the presently disclosed method for quantifying protein conjugated to a nanoparticle, such as a cadmium selenium (CdSe) nanoparticle having a zinc sulfite coating and a polymer outercoating. Protein conjugated to the nanoparticle is digested enzymatically, such as by using Proteinase K, a 28.9 kDA endolytic serine protease that cleaves peptide bonds to produce both free peptides and/or amino acids. Enzymatic digestion also liberates the nanoparticle, which can be separated, at least substantially, from the biomolecules using known suitable methods, such as centrifugation. If necessary, the reaction mixture produced by the digestion/digestion step can be quenched, such as by using an acid, as indicated in FIG. 1. Concentrations of peptides and/or amino acids are determined using tryptophan fluorescence by comparison to a standard fluorescence versus concentration curve.

Figure 2:
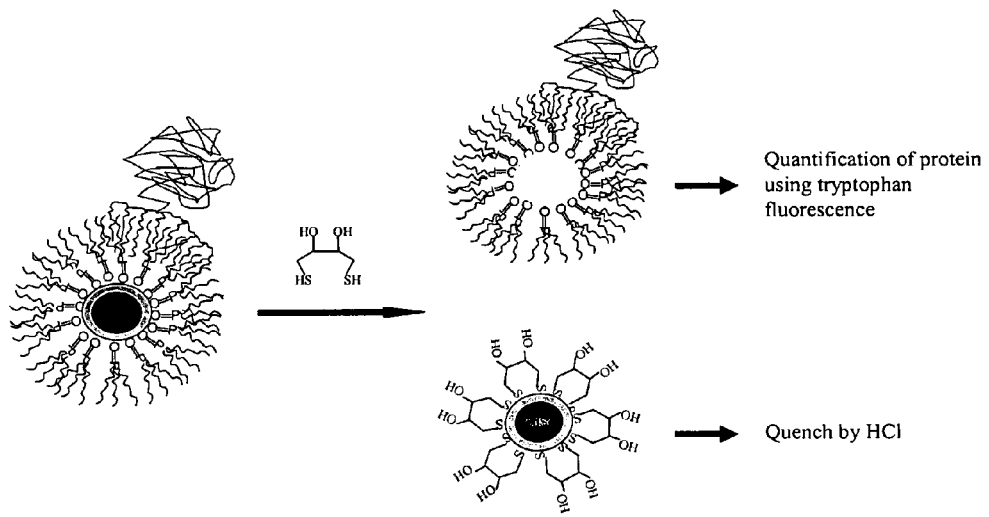
FIG. 2 schematically illustrates one embodiment of a method for quantifying proteins conjugated to a nanoparticle using ligand exchange and fluorescence spectroscopy.

FIG. 2 schematically illustrates another working embodiment for quantifying biomolecules conjugated to a nanoparticle. For the embodiment of FIG. 2, ligand displacement can be used to displace the polymeric material and associated biomolecules from the nanoparticle.

Compounds having a single functional group suitable for ligand displacement, such as monothiols, can be used for ligand displacement. But, compounds having plural functional groups, such as polythiols, are more efficient for this process. Suitable additional exemplary ligand displacing compounds include amines, polyamines, phosphines, phosphine oxides, alkyl phosphines, derivatized alkyl phosphines, alkyl phosphine oxides, derivatized alkyl phosphine oxides, thiols, and combinations thereof. FIG. 2 illustrates using a dithiol, such as threo-1,4-dimercaptobutane-2,3-diol (dithiothreitol), shown below, or similar compounds, such as erythritol, dierythritol, trierythritol, pentaerythritol, dipentaerythritol, tripentaerythritol, dihydrolipoic acid, etc. to displace the bound polymer.

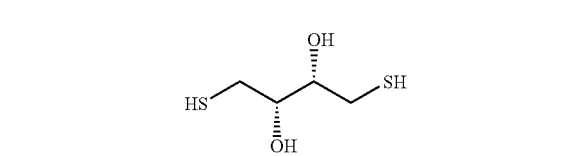

The released biomolecule is then quantified spectrophotometrically, such as by tryptophan fluorescence.

Figure 3:
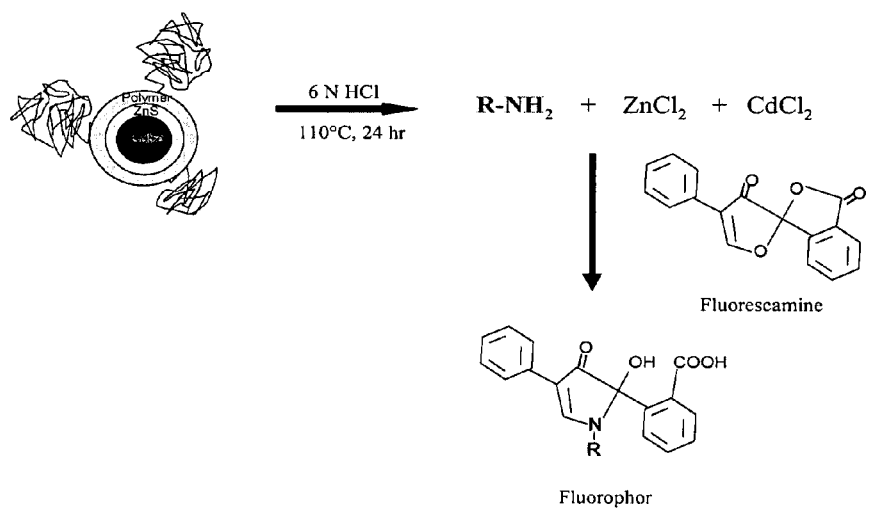
FIG. 3 schematically illustrates one embodiment of a method for quantifying proteins conjugated to a nanoparticle using chemical digestion and fluorimetric quantification of amino acid using reactive compound fluorescamine.
Figure 4:
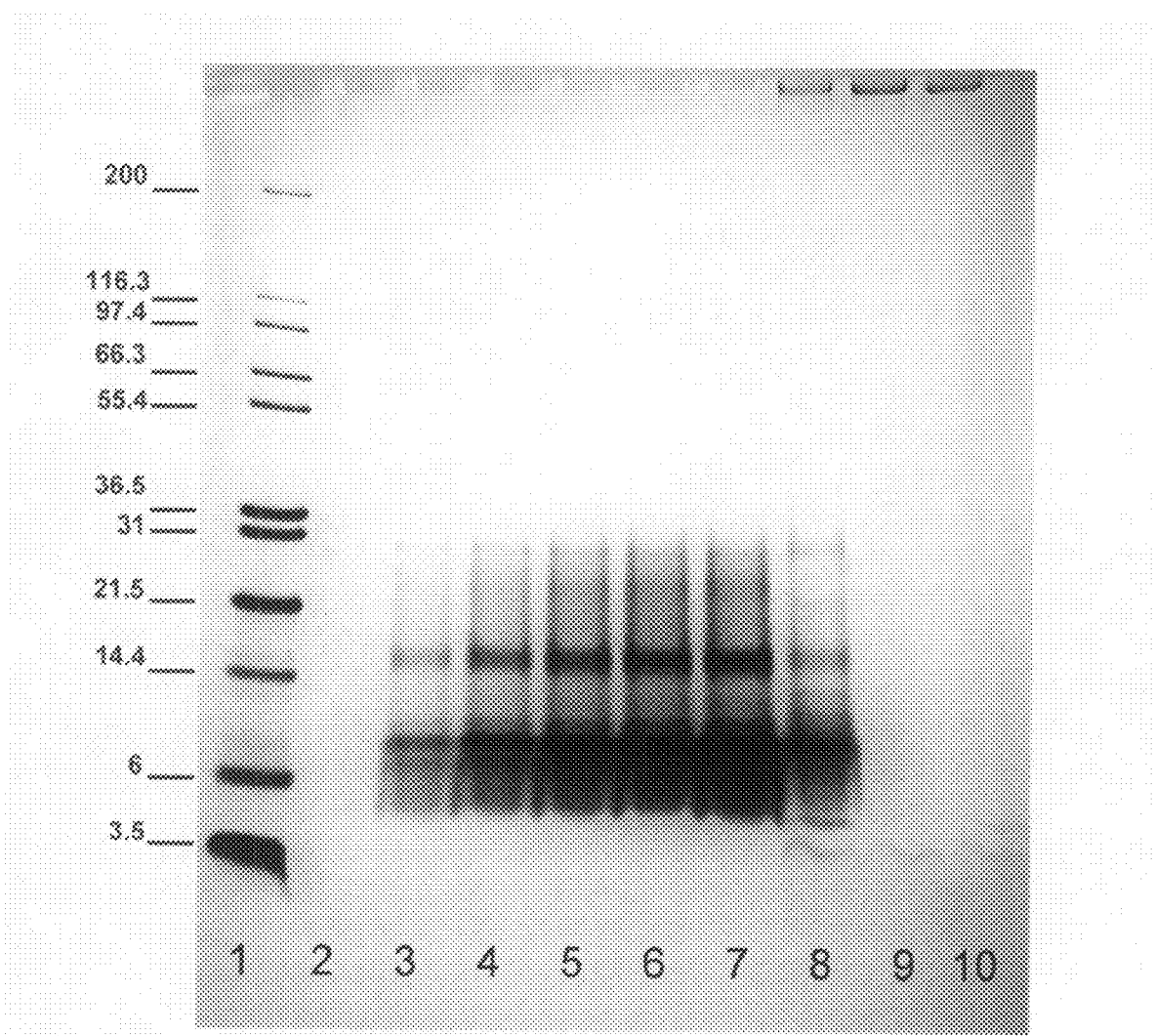
FIG. 4 is a photomicrograph of a silver staining of SDS-PAGE gel of Proteinase K digestion products of goat anti mouse IgG, Q655 Qdots and Q655 goat anti mouse IgG conjugate.

FIG. 3 schematically illustrates yet another working embodiment of the present invention that involves chemical digestion, as opposed to enzymatic digestion or ligand displacement. FIG. 3 specifically illustrates using a mineral acid, such as hydrochloric acid, to form amino acids from proteins. Amines are relatively reactive, and hence can react with another molecule selected for its ability to facilitate quantification of the amino acids, such as by producing spectrophotometrically detectable moieties. FIG. 3 specifically illustrates using fluorescamine, a common fluorogen, for reaction with the amino acids and/or peptides in a reaction mixture. A standard curve is produced by using incrementally variable concentrations of the biomolecule. The standard curve is then used to determine concentrations of amino acid-peptide fluorophore adducts in actual reaction mixtures.

VI. EXAMPLES

The following examples are provided to exemplify certain features of working embodiments. A person of ordinary skill in the art will appreciate that the scope of the invention is not limited to the particular features disclosed by such examples.

Example 1

This example concerns a working embodiment of a method for enzymatically digesting IgG molecules, a monomeric immunoglobulin, from a Q655 goat anti mouse IgG bioconjugate. 30 pmoles of the conjugate were digested overnight with 250 ng of Proteinase K in 500 μl of buffer containing 50 mM sodium borate, 0.5% SDS and 2.5 mM calcium chloride, pH 8.3 at 37° C. Digestion products were then quenched with 20 μl of 6N HCl for 3 hours at ambient temperature. Nanoparticles were separated from protein fragments by centrifugation for 5 minutes at 12,000 rpm. The supernatant was neutralized with NaOH to pH 8.0. Tryptophan fluorescence of the supernatant was taken under the following parameters: excitation at 270 nm, emission peak from 300 nm to 400 nm.

Figure 5:
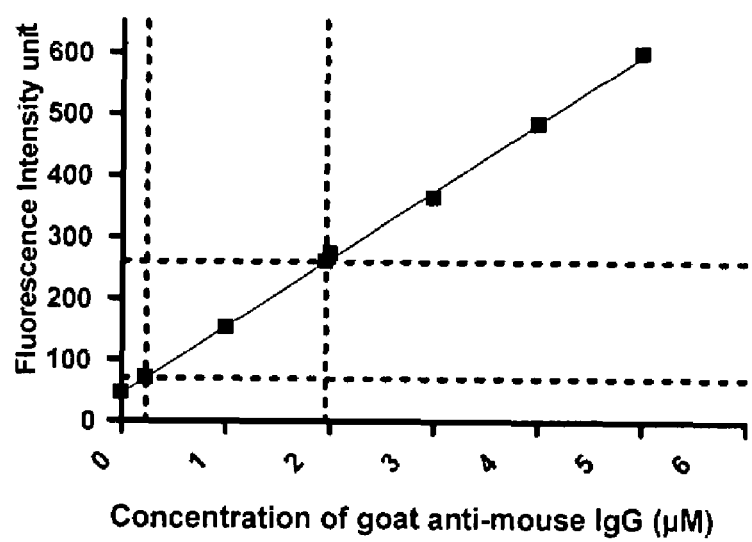
FIG. 5 is a curve of fluorescence intensity versus goat anti-mouse IgG concentration (μM) illustrating quantification of goat anti mouse IgG molecules conjugated to Q655 quantum dots using Proteinase K degradation followed by quantification of degradation product by tryptophan fluorescence spectroscopy.

A standard tryptophan fluorescence curve was used to determine the amount of protein bound to the nanoparticle. FIG. 5 provides the curve of fluorescence intensity units versus molar concentration of goat anti-mouse IgG. For this example, the background fluorescence contributed by the Q655 nanoparticle and linker was subtracted from the total fluorescence. Hydrochloric acid was added to completely quench the fluorescence of nanoparticles and centrifugation provided a method for removing liberated nanoparticles. As a result, the fluorescence contribution to the mixture by the nanoparticle must be accounted for to provide a more accurate representation of the number of biomolecules conjugated to a nanoparticle. For this particular example, the nanoparticle contribution was subtracted to provide a fluorescence measurement corresponding to a protein concentration in the sample of about 1.8 micromolar. The concentration of the nanoparticle in the sample was known to be 1 micromolar based on the absorbance, using the molar extinction coefficient for Q655 dotes, where E=800,000 m$^{-1}$cm$^{-1}$. Nanoparticle concentration was initially determined using the molar extinction coefficient $\epsilon$ of a chemical species at a given wavelength. The molar extinction coefficient is a measure of how strongly the species absorbs light at that wavelength. For N components with concentrations $c_i$ (i=1, . . . , N) and N wavelengths $\lambda_i$, absorbances $A_i$ are obtained:

$$A(\lambda_i) = L \sum_{j=1}^{N} \epsilon_j(\lambda_i) c_j.$$

This set of equations can be solved for the concentration $c_j$, provided that none of the wavelengths is an isosbestic point for any pair of species, i.e. a wavelength where the two species have equal extinction coefficients. Thus, by dividing the biomolecule concentration (1.8 micromolar) as determined by fluorescence spectroscopy by the known nanoparticle concentration (1 micromolar), it was determined that nanoparticles of this particular example had about 1.8 protein molecules per nanoparticle.

Example 2

30 pmoles of nanoparticle bioconjugate comprising a Q655 goat anti mouse IgG bioconjugate were heated to reflux in 500 μl of buffer containing 50 mM sodium borate, 0.1% SDS, and 50 mM DTT for 30 minutes to allow ligand exchange. The reaction was quenched with hydrochloric acid and nanoparticles were substantially separated from the reaction mixture by centrifugation. The supernatant was neutralized with sodium hydroxide. Tryptophan fluorescence spectra were taken of the reaction mixture as described in Example 1. A standard curve also was generated using free IgG treated in the same way as with the IgG-nanoparticle conjugate.

Figure 6:
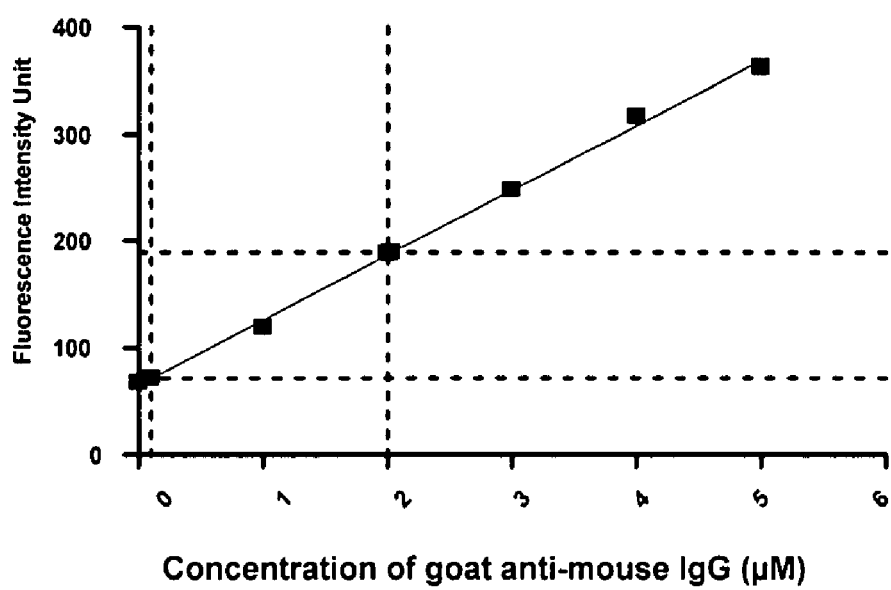
FIG. 6 is a curve of fluorescence intensity versus goat anti-mouse IgG concentration (μM) illustrating quantification of goat anti mouse IgG molecules conjugated to Q655 quantum dots using DTT ligand exchange followed by quantification of ligand exchange product by tryptophan fluorescence spectroscopy.

FIG. 6 is a fluorescence intensity curve versus molar concentration of goat anti-mouse IgG. For this example, the background fluorescence contributed by Q655 nanoparticles corresponded to about a 0.1 micromolar nanoparticle concentration. This background fluorescence was subtracted from the total fluorescence of the bioconjugate (2.0 concentration) to provide a protein concentration of about 1.9 micromolar, or about 1.9 molecules of IgG per Q655 nanoparticle.

Example 3

15 pmoles of a Q655 goat anti mouse IgG bioconjugate were digested with 6N HCl at 110° C. for 24 hours. The reaction was then neutralized to pH 8.0 with NaOH. The released amino acids were then reacted with fluorescamine at a pH of from about 7 to about 9 in a buffered solution that did not include an amine, such as PBS and sodium borate buffers that have a pH range of from about 7 to about 9.

Figure 7:
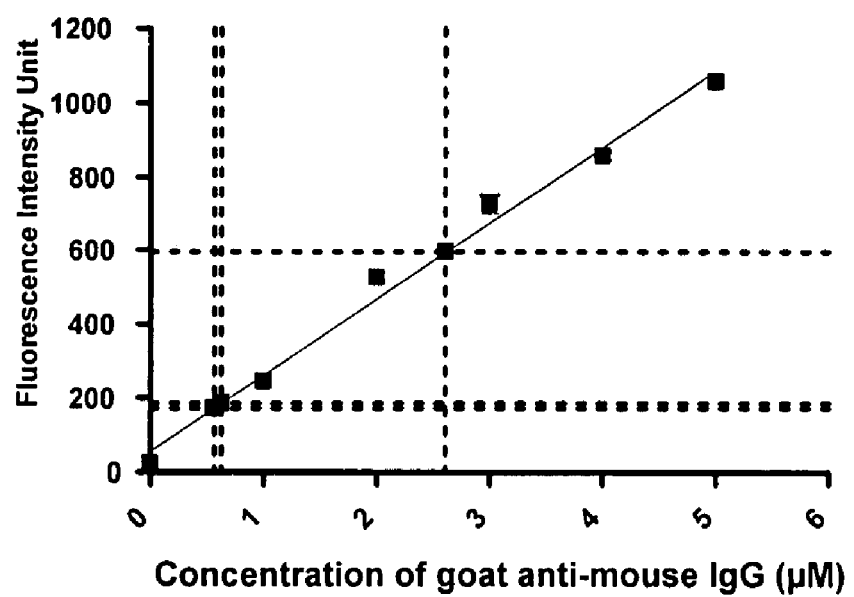
FIG. 7 is a curve of fluorescence intensity versus goat anti-mouse IgG concentration (μM) illustrating quantification of goat anti mouse IgG molecule conjugated to Q655 quantum dotes using hydrochloric acid degradation followed by fluorimetric quantification of amino acid using fluorescamine.

A standard curve was produced using free goat anti-mouse IgG treated in the same way as the Q-dot conjugates. FIG. 7 illustrates that the total fluorescence for the sample of this example corresponded to a concentration of 2.6 micromolar. The 0.56 fluorescence contribution of the Q655 nanoparticle and PEG12 linker (0.56) was subtracted from the total fluorescence to provide a protein concentration of about 2 micromolar. As discussed above, because the nanoparticle concentration of the original sample was known to be about 1 micromolar, the number of biomolecules per nanoparticle was calculated to about 2 molecules of goat anti mouse IgG to the Q655 nanoparticle.

Example 4

15 pmoles of Q605 goat anti rabbit IgG conjugate, affinity bound conjugate, and affinity unbound conjugate were digested with 6N HCl at 110° C. for 24 hours respectively. The reactions were then neutralized to pH 8.0 with sodium hydroxide. The released amino acids were then reacted with fluorescamine. A standard curve was generated using a series of concentrations of free goat anti rabbit IgG molecules treated the same way as the Qdot conjugates.

Figure 8:
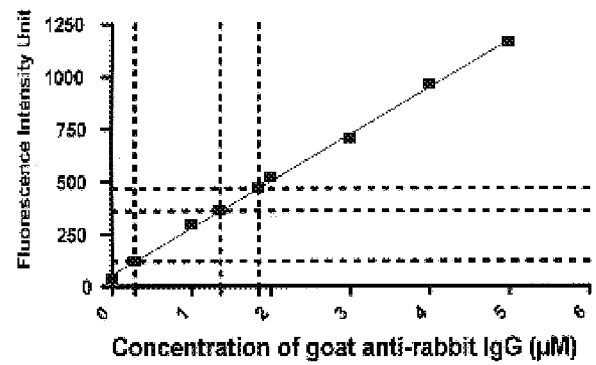
FIG. 8 is a curve of fluorescence intensity versus goat anti-rabbit IgG concentration (μM) illustrating quantification of affinity purified and non-purified goat anti rabbit IgG Q605 conjugates using hydrochloric acid degradation followed by fluorimetric quantification of amino acid using fluorescamine.

FIG. 8 is a curve of fluorescence intensity versus goat anti rabbit IgG concentration (μM). For this example, after subtraction of the background fluorescence contributed by Q605 and PEG12 linker (0.3 μM), the Q605 goat anti rabbit conjugate shows about 1.1 (1.4-0.3) molecules per dot; the affinity bound conjugate has 1.6 (1.9-0.3) molecules per dot; and the affinity unbound conjugate has 0 (0.3-0.3) molecules per dot.

Figure 9:
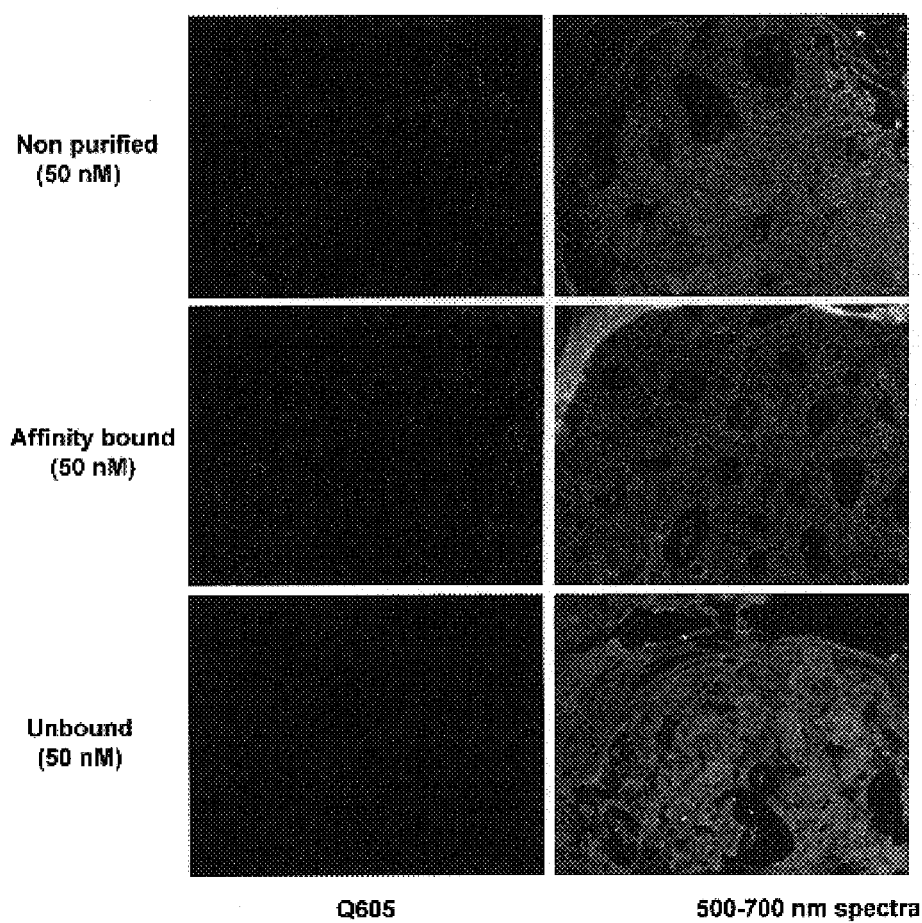
FIG. 9 is a photomicrograph of CD20 immunostaining of tonsil tissue using non-purified Q605 goat anti rabbit IgG conjugate, affinity bound conjugates, and unbound conjugates, where the left panels are images taken at Q605 emission wavelength, and the right panels are image spectrum from 500 nm to 700 nm.

FIG. 9 is a photomicrograph of CD20 immunostaining of tonsil tissue using Q605 goat anti rabbit IgG conjugate, affinity bound conjugate, and unbound conjugate. Left panels are images taken at the Q605 emission wavelength. The right panels are image spectrum from 500 nm to 700 nm. Both non-purified conjugate and affinity-bound conjugate show specific membrane staining. Affinity unbound conjugate shows essentially no specific staining, which is consistent with the quantification results.

Example 5

This example concerns a working embodiment of a method for enzymatically digesting a biomolecule-nanoparticle conjugate comprising streptavidin (a tetrameric protein purified from *Streptomyces avidinii*) conjugated to a Q605 nanoparticle. 30 pmoles of the conjugate were digested overnight with 250 ng of Proteinase K in 500 μl of buffer containing 50 mM sodium borate, 0.5% SDS and 2.5 mM calcium chloride, pH 8.3 at 37° C. Digestion products were then quenched with 20 µl of 6N HCl for 3 hours at ambient temperature. Nanoparticles were substantially separated from protein fragments by centrifugation for 5 minutes at 12,000 rpm. The supernatant was neutralized with NaOH to pH 8. Tryptophan fluorescence of the supernatant was taken under the following parameters: excitation at 270 nm, emission peak from 300 nm to 400 nm.

Figure 10:
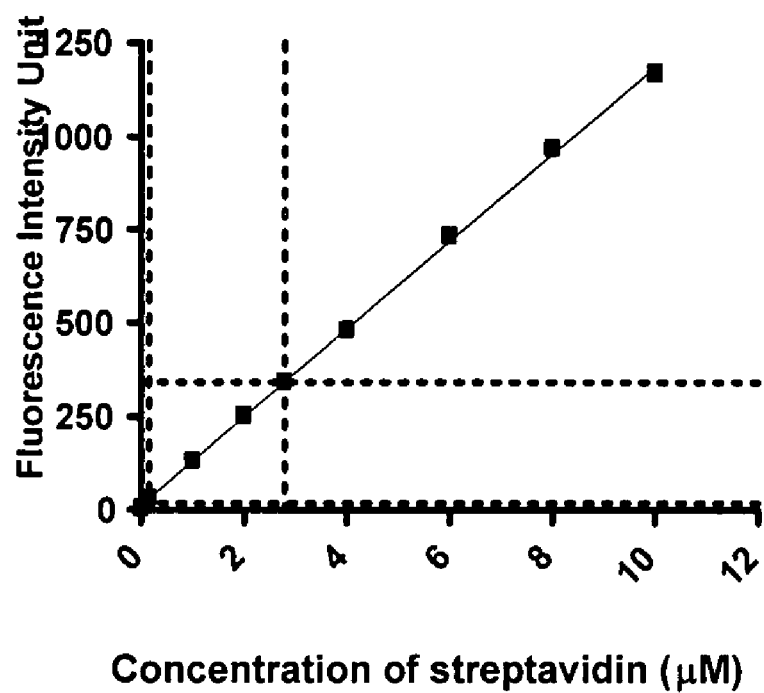
FIG. 10 is a curve of fluorescence intensity versus streptavidin concentration (μM) illustrating quantification of streptavidin conjugated to Q605 quantum dots using Proteinase K degradation followed by quantification of degradation products by tryptophan fluorescence spectroscopy.

A standard tryptophan fluorescence curve was used to determine the amount of protein bound to the nanoparticle. FIG. 10 is a fluorescence intensity versus streptavidin concentration curve (µM). For this example, the background fluorescence contributed by Q605 nanoparticle alone corresponded to a concentration of about 0.2 µM, the fluorescence of Q605 streptavidin conjugate corresponded to a concentration of about 2.8 µM, which indicates that the protein concentration was about 2.6 (2.79-0.158) µM, or 2.6 molecules of streptavidin per Q605 nanoparticle based on the original, known 1.0 µM nanoparticle concentration.

Example 6

30 pmoles of a streptavidin-Q605 nanoparticle were heated to reflux in 500 µl of buffer containing 50 mM sodium borate, 0.1% SDS, and 50 mM DTT for 30 minutes to allow ligand exchange. The reaction was quenched with hydrochloric acid and neutralized.

Figure 11:
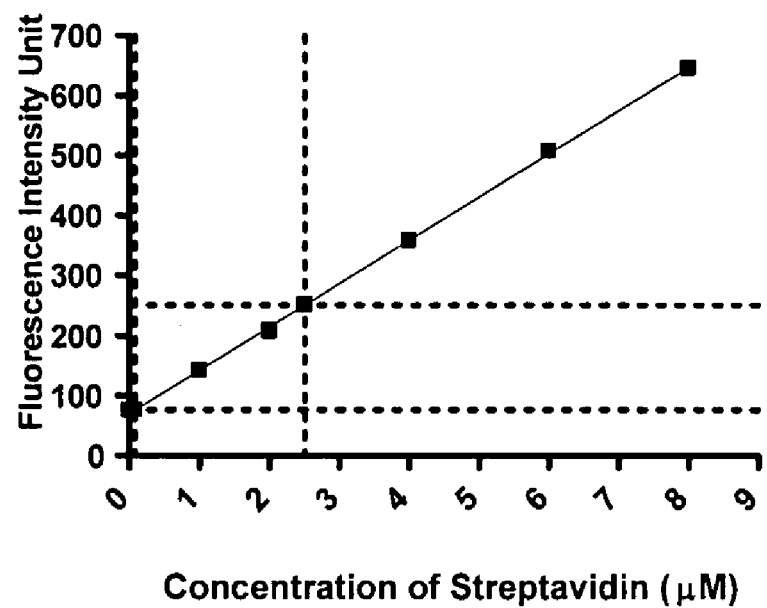
FIG. 11 is a curve of fluorescence intensity versus streptavidin concentration (μM) illustrating quantification of streptavidin conjugated to Q605 quantum dots using DTT ligand exchange followed by quantification of ligand exchange products by tryptophan fluorescence spectroscopy.

A standard curve was used to determine the amount of streptavidin bound to the nanoparticle using tryptophan fluorescence. FIG. 11 is a fluorescence intensity versus micromolar streptavidin concentration. For this example, the background fluorescence contributed by Q605 and $PEG_{12}$ linker corresponded to a concentration of about 0.08 µM, and the fluorescence for the entire reaction mixture corresponded to about 2.8 µM. Subtracting the two indicates that the streptavidin concentration was about 2.4 µM (2.5 µM-0.08 µM), or 2.4 molecules of streptavidin per Q605 nanoparticle based on the original, known 1.0 µM nanoparticle concentration.

Example 7

15 pmoles of a streptavidin-Q605 nanoparticle conjugate were chemically degraded using 6N HCl at 110° C. for 24 hours. The reaction was then neutralized to pH 8.0 with 10N NaOH. For this example, there is no need to separate nanoparticles, as they are substantially dissolved by the 6N HCl.

Figure 12:
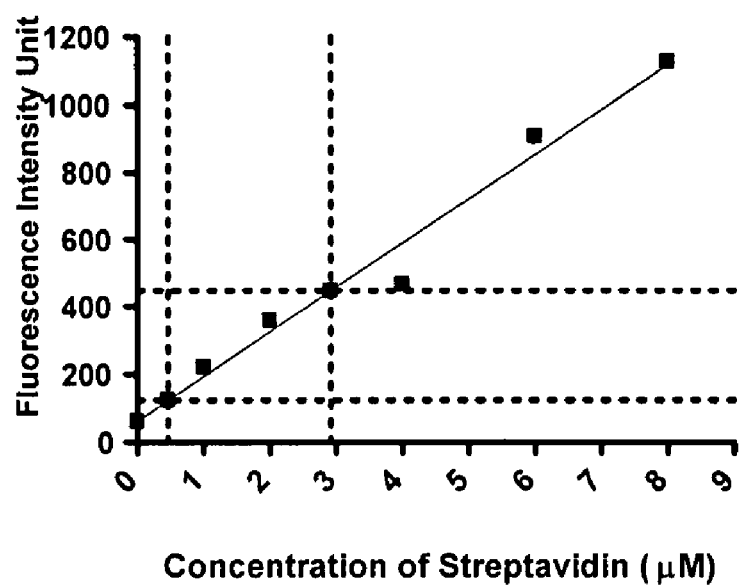
FIG. 12 is a curve of fluorescence intensity versus streptavidin concentration (μM) illustrating quantification of streptavidin conjugated to Q605 quantum dots using hydrochloric acid degradation followed by fluorimetric quantification of amino acid using fluorescamine.

Streptavidin digestion products were reacted with fluorescamine. A standard curve was then used to determine the amount of streptavidin bound to the nanoparticle by fluorimetric quantification of amino acids using fluorescamine. FIG. 12 is a fluorescence intensity curve versus streptavidin concentration (µM). For this example, background fluorescence contributed by the Q605 nanoparticle and $PEG_{12}$ linker corresponded to about 0.5 µM, and the fluorescence for the streptavidin-bioconjugate reaction mixture corresponded to about 3.0 µM. Thus, the protein concentration in the reaction sample was about 2.4 µM (2.9 µM-0.5 µM), or 2.4 molecules of streptavidin per Q605 nanoparticle based on the original, known 1.0 µM nanoparticle concentration.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for quantifying a biomolecule conjugated to a nanoparticle, comprising:
   providing a bioconjugate comprising a nanoparticle having a nucleic acid conjugated thereto;
   providing a complementary nucleic acid strand labeled with a fluorophore;
   hybridizing the complementary nucleic acid strand with nucleic acid of a nucleic acid-nanoparticle bioconjugate to form a nucleic acid complementary strand hybridization product;
   quenching nanoparticle fluorescence using a mineral acid or a transition metal; and
   detecting hybridization products and quantifying numbers of nucleic acid molecules conjugated to the nanoparticle by comparing fluorescence intensity produced by the fluorophore to a standard concentration curve generated using the nucleic acid-complementary strand hybridization product to determine nucleic acid concentration.

2. A method for quantifying protein conjugated to a nanoparticle, comprising:
   providing a bioconjugate comprising a nanoparticle having a protein conjugated thereto;
   displacing the protein conjugated to the nanoparticle to produce a displaced protein; and
   quantifying protein concentration spectrophotometrically using tryptophan fluorescence.

3. A method for quantifying a biomolecule conjugated to a nanoparticle, comprising:
   providing a bioconjugate comprising an antibody conjugated to a quantum dot;
   heating a reaction mixture comprising the bioconjugate in a solution comprising a thiol ligand exchange compound; and
   measuring tryptophan fluorescence to determine antibody concentration.

4. A method for assessing signal generation capabilities of biomolecule-nanoparticle conjugates, comprising:
   providing a first bioconjugate and a second bioconjugate, each of the first and second bioconjugates comprising a biomolecule conjugated to a nanoparticle, the first and second bioconjugates having first and second different biomolecule-to-nanoparticle ratios that are determined by quantifying the biomolecule conjugated to the nanoparticle by first digesting the biomolecule or by forming a hybridization product of the biomolecule;
   assessing the first bioconjugate for an assay function to provide a first assessment;
   assessing the second bioconjugate for the assay function to provide a second assessment; and
   comparing the first and second assessments, thereby assessing signal generation capabilities of the first and second bioconjugates.

5. The method according to claim 4 where the assay function comprises signal generation in an immunohistochemical assay or an in situ hybridization assay.

6. The method according to claim 5 where the assay function comprises signal generation in a multiplexed assay.

7. The method according to claim 4 where quantifying comprises removing the biomolecule from the nanoparticle.

8. The method according to claim 4 where quantifying comprises determining the number of biomolecules conjugated to the nanoparticle.

9. The method according to claim 4 where the biomolecules are amino acids, peptides, proteins, nucleic acids, oligonucleotides, DNA, RNA, or combinations thereof.

10. A method for quantifying protein conjugated to a nanoparticle, comprising:
displacing, and optionally digesting, protein from a protein-nanoparticle conjugate to produce displaced protein;
substantially separating the nanoparticle from the displaced protein; and
spectrophotometrically determining a displaced protein concentration using tryptophan fluorescence.

11. The method according to claim 10 where substantially separating comprises centrifugation.

12. The method according to claim 10 further comprising enzymatically digesting protein conjugated to the nanoparticle using an enzyme selected from proteinase K, trypsin, clostripain, staphylococcal protease, subtilisin, thrombin, chymotrypsin, carboxypeptidase a, or combinations thereof.

13. The method according to claim 10 where the nanoparticle is a coated quantum dot, and the method further comprises displacing protein from the nanoparticle by ligand exchange using an amine, a polyamine, a phosphine, a phosphine oxide, an alkyl phosphine, a derivatized alkyl phosphine, an alkyl phosphine oxide, a derivatized alkyl phosphine oxide, a thiol, or a combination thereof.

14. The method according to claim 10 where the nanoparticle is an alloyed quantum dot.

15. The method according to claim 10 where the protein is an antibody, an antibody fragment, a genetically engineered antibody, a chimeric antibody, a heteroconjugate antibody, or a combination thereof.

16. The method according to claim 10 where the protein is IgA, IgD, IgE, IgG, IgM, avidin, streptavidin, or a combination thereof.

17. The method according to claim 10 where the protein is a proteolytic antibody fragment, a recombinant antibody fragment, a diabody, a triabody, a chimeric antibody, or a combination thereof.

18. The method according to claim 10 where the protein is an F(ab')$_2$ fragment, an Fab' fragment, an Fab'-SH fragment, a Fab fragment, an sFv fragment, a dsFv fragment, a bispecific sFv fragment, a bispecific dsFv fragment, a single chain Fv protein ("scFv"), a disulfide stabilized Fv protein, or a combination thereof.

19. The method according to claim 10 where the protein is displaced either simultaneously with or following a digestion process to produce smaller constituent units.

20. The method according to claim 10 further comprising:
reacting displaced protein with a compound to form a detectable moiety; and
determining detectable moiety concentrations.

21. The method according to claim 1 where quantifying comprises determining the number of nucleic acids that are conjugated to the nanoparticle.

22. The method according to claim 1 where the nanoparticle is a quantum dot having a trioctylphosphine (TOP) or trioctylphosphine oxide (TOPO) ligand.

23. The method according to claim 1 where the nucleic acid is a gene, a viral RNA, a viral DNA, a bacterial DNA, a fungal DNA, a cDNA, an mRNA, an RNA or a DNA fragment, an oligonucleotide, a synthetic oligonucleotide, a modified oligonucleotide, a single-stranded or double-stranded nucleic acid, or a natural or synthetic nucleic acid.

24. The method according to claim 1 where the nanoparticle is a quantum dot, a paramagnetic nanoparticle, a superparamagnetic nanoparticle, or a metal nanoparticle.

25. The method according to claim 1 where the nanoparticle is an alloyed quantum dot.

26. The method according to claim 1 where the nanoparticle comprises CdSe, ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs or InGaN.

27. The method according to claim 2 where quantifying comprises determining the number of protein molecules conjugated to the nanoparticle.

28. The method according to claim 2 further comprising digesting the protein chemically and/or using an enzyme.

29. The method according to claim 28 where the enzyme is proteinase K, trypsin, clostripain, staphylococcal protease, subtilisin, thrombin, chymotrypsin, carboxypeptidase a, pepsin, papain, or combinations thereof.

30. The method according to claim 2 where displacing the protein comprises displacing proteins by ligand exchange.

31. The method according to claim 30 where the nanoparticle is a quantum dot having a trioctylphosphine (TOP) or trioctylphosphine oxide (TOPO) ligand, and ligand exchange is performed using an amine, polyamine, phosphine, phosphine oxide, alkyl phosphine, derivatized alkyl phosphine, alkyl phosphine oxide, derivatized alkyl phosphine oxide, thiol, or combinations thereof.

32. The method according to claim 30 comprising ligand exchange using a polythiol.

33. The method according to claim 30 comprising ligand exchange using dithiothreitol, erythritol, dierythritol, trierythritol, pentaerythritol, dipentaerythritol, tripentaerythritol, dihydrolipoic acid, or combinations thereof.

34. The method according to claim 2 where the nanoparticle is a quantum dot, an alloyed quantum dot, a paramagnetic nanoparticle, a superparamagnetic nanoparticle, or a metal nanoparticle.

35. The method according to claim 2 where the nanoparticle comprises CdSe, ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs or InGaN.

36. The method according to claim 2 where the protein is an antibody, an antibody fragment, a genetically engineered antibody, a diabody, a triabody, a chimeric antibody, a heteroconjugate antibody, or a combination thereof.

37. The method according to claim 2 where the protein is an IgA, an IgD, an IgE, an IgG, an IgM, an avidin, a streptavidin, or a combination thereof.

38. The method according to claim 2 where the protein is an F(ab')$_2$ fragment, an Fab' fragment, an Fab'-SH fragment, a Fab fragment, an sFv fragment, a dsFv fragment, a bispecific sFv fragment, a bispecific dsFv fragment, a single chain Fv protein ("scFv"), a disulfide stabilized Fv protein, or a combination thereof.

39. The method according to claim 2 where the protein is displaced either simultaneously with or followed by an enzymatic digestion, a chemical digestion, a physical digestion, or a combination thereof, to produce smaller constituent units.

40. The method according to claim 2 further comprising:
reacting the displaced protein with a compound to form a detectable moiety; and
determining a concentration of the detectable moiety.

41. The method according to claim 2 where the protein is an immunoglobulin, the nanoparticle is a quantum dot, and the bioconjugate is digested using Proteinase K.

42. The method according to claim 2 where the protein is streptavidin or an immunoglobulin, the nanoparticle is a quantum dot, the bioconjugate is digested with an acid, released amino acids are reacted with fluorescamine, and protein concentration is determined using fluorescence spectroscopy.

43. The method according to claim 3 where the thiol ligand exchange compound comprises dithiothreitol, erythritol, dierythritol, trierythritol, pentaerythritol, dipentaerythritol, tripentaerythritol, dihydrolipoic acid, or combinations thereof.

44. The method according to claim 3 where the nanoparticle is a quantum dot, an alloyed quantum dot, a paramagnetic nanoparticle, a superparamagnetic nanoparticle, or a metal nanoparticle.

45. The method according to claim 3 where the nanoparticle comprises CdSe, ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs or InGaN.

46. The method according to claim 3 where the antibody is an antibody fragment, a genetically engineered antibody, a diabody, a triabody, a chimeric antibody, a heteroconjugate antibody, or a combination thereof.

47. The method according to claim 3 where the antibody is an IgA, an IgD, an IgE, an IgG, an IgM or a combination thereof.

48. The method according to claim 3 where the antibody is an F(ab')$_2$ fragment, an Fab' fragment, an Fab'-SH fragment, a Fab fragment, an sFv fragment, a dsFv fragment, a bispecific sFv fragment, a bispecific dsFv fragment, a single chain Fv protein ("scFv"), a disulfide stabilized Fv protein, or a combination thereof.

49. The method according to claim 4 where quantifying comprises determining the number of biomolecules conjugated to the nanoparticle.

50. The method according to claim 4 where the biomolecule is a protein, and the method further comprises digesting the protein chemically and/or enzymatically.

51. The method according to claim 4 and further comprising using a detectable label to detect digestion products.

52. The method according to claim 51 where the digestion products include free amines that react with a detectable label selected from fluorescamine, 3-(4- carboxybenzoyl)quinoline-2-carboxaldehyde, o-phthaldialdehyde, or a combination thereof.

53. The method according to claim 51 where the detectable label is an intrinsic fluorophore.

54. The method according to claim 53 where the fluorophore is Texas Red, fluorescein isothiocyanate, 2',7'-difluorofluorescein, coumarin, or combinations thereof.

55. The method according to claim 50 comprising using an enzyme selected form proteinase K, trypsin, clostripain, staphylococcal protease, subtilisin, thrombin, chymotrypsin, carboxypeptidase a, pepsin, papain, or a combination thereof.

56. The method according to claim 4 further comprising determining biomolecule concentrations spectrophotometrically.

57. The method according to claim 4 further comprising determining biomolecule concentrations fluorimetrically.

58. The method according to claim 4 where the biomolecule is a protein and quantifying comprises measuring tryptophan fluorescence.

59. The method according to claim 4 comprising displacing biomolecules by ligand exchange, the nanoparticle is a quantum dot having a trioctylphosphine (TOP) or trioctylphosphine oxide (TOPO) ligand, and ligand exchange is performed using an amine, polyamine, phosphine, phosphine oxide, alkyl phosphine, derivatized alkyl phosphine, alkyl phosphine oxide, derivatized alkyl phosphine oxide, thiol, or a combination thereof.

60. The method according to claim 59 comprising ligand exchange using dithiothreitol, erythritol, dierythritol, trierythritol, pentaerythritol, dipentaerythritol, tripentaerythritol, dihydrolipoic acid, or combinations thereof.

61. The method according to claim 4 where the biomolecule is an antibody, an antibody fragment, a recombinant antibody fragment, a genetically engineered antibody, a diabody, a triabody, a chimeric antibody, a heteroconjugate antibody, or a combination thereof.

62. The method according to claim 4 where the biomolecule is an IgA, an IgD, an IgE, an IgG, an IgM, an avidin, a streptavidin, or a combination thereof.

63. The method according to claim 4 where the biomolecule is an F(ab')$_2$ fragment, an Fab' fragment, an Fab'-SH fragment, a Fab fragment, an sFv fragment, a dsFv fragment, a bispecific sFv fragment, a bispecific dsFv fragment, a single chain Fv protein ("scFv"), a disulfide stabilized Fv protein, or a combination thereof.

64. The method according to claim 4 further comprising:
displacing the biomolecules conjugated to the nanoparticles to produce displaced biomolecules; and
determining a concentration of the displaced biomolecules.

65. The method according to claim 64 where the biomolecules are displaced either simultaneously with or followed by a digestion process to produce smaller constituent units.

66. The method according to claim 65 where the digestion process is an enzymatic digestion, a chemical digestion, a physical digestion, or a combination thereof.

67. The method according to claim 4 further comprising:
displacing a biomolecule conjugated to the nanoparticle from the nanoparticle to produce a displaced biomolecule;
reacting the displaced biomolecule with a compound to form a detectable moiety; and
determining a concentration of the detectable moiety.

68. The method according to claim 4 where the biomolecules are immunoglobulins conjugated to quantum dots, the conjugate is digested using Proteinase K, and tryptophan fluorescence is used to determine a concentration of the immunoglobulin.

69. The method according to claim 4 where the biomolecules are streptavidin or immunoglobulins conjugated to quantum dots, a reaction mixture comprising the bioconjugate is digested with an acid, released amino acids are reacted with fluorescamine, and a streptavidin or immunoglobulin concentration is determined using fluorescence spectroscopy.

* * * * *